United States Patent
Li et al.

(10) Patent No.: US 10,468,244 B2
(45) Date of Patent: Nov. 5, 2019

(54) PRECURSORS AND FLOWABLE CVD METHODS FOR MAKING LOW-K FILMS TO FILL SURFACE FEATURES

(71) Applicant: Versum Materials US, LLC, Allentown, PA (US)

(72) Inventors: Jianheng Li, Santa Clara, CA (US); Raymond Nicholas Vrtis, Orefield, PA (US); Robert Gordon Ridgeway, Quakertown, PA (US); Manchao Xiao, San Diego, CA (US); Xinjian Lei, Vista, CA (US)

(73) Assignee: VERSUM MATERIALS US, LLC, Tempe, AZ (US)

( * ) Notice: Subject to any disclaimer, the term of this patent is extended or adjusted under 35 U.S.C. 154(b) by 37 days.

(21) Appl. No.: 15/681,102

(22) Filed: Aug. 18, 2017

(65) Prior Publication Data

US 2018/0061636 A1 Mar. 1, 2018

Related U.S. Application Data

(60) Provisional application No. 62/381,222, filed on Aug. 30, 2016.

(51) Int. Cl.
| | |
|---|---|
| *H01L 21/02* | (2006.01) |
| *C01B 33/12* | (2006.01) |
| *C07F 7/18* | (2006.01) |
| *C09D 1/00* | (2006.01) |
| *C23C 16/50* | (2006.01) |
| *C23C 16/56* | (2006.01) |
| *C09D 7/61* | (2018.01) |
| *C23C 16/04* | (2006.01) |
| *C23C 16/40* | (2006.01) |

(52) U.S. Cl.
CPC ...... *H01L 21/02211* (2013.01); *C01B 33/126* (2013.01); *C07F 7/1896* (2013.01); *C09D 1/00* (2013.01); *C09D 7/61* (2018.01); *C23C 16/045* (2013.01); *C23C 16/401* (2013.01); *C23C 16/50* (2013.01); *C23C 16/56* (2013.01); *H01L 21/02126* (2013.01); *H01L 21/02203* (2013.01); *H01L 21/02214* (2013.01); *H01L 21/02216* (2013.01); *H01L 21/02274* (2013.01); *H01L 21/02348* (2013.01)

(58) Field of Classification Search
CPC ......... H01L 21/02214; H01L 21/02219; H01L 21/02126; H01L 21/0234; H01L 21/02348; H01L 21/02274; C07F 7/1896
See application file for complete search history.

(56) References Cited

U.S. PATENT DOCUMENTS

| | | | |
|---|---|---|---|
| 6,825,130 B2 | 11/2004 | Todd | |
| 6,846,515 B2 | 1/2005 | Vrtis et al. | |
| 7,074,690 B1 | 7/2006 | Gauri et al. | |
| 7,098,149 B2 | 8/2006 | Lukas et al. | |
| 7,384,471 B2 | 6/2008 | Vrtis et al. | |
| 7,404,990 B2 | 7/2008 | Lukas et al. | |
| 7,468,290 B2 | 12/2008 | Lukas et al. | |
| 7,498,273 B2 | 3/2009 | Mallick et al. | |
| 7,521,378 B2 | 4/2009 | Fucsko et al. | |
| 7,541,297 B2 | 6/2009 | Mallick et al. | |
| 7,557,420 B2 | 7/2009 | Fucsko et al. | |
| 7,582,555 B1 | 9/2009 | Lang et al. | |
| 7,825,040 B1 | 11/2010 | Fukazawa et al. | |
| 7,888,233 B1 | 2/2011 | Gauri et al. | |
| 7,915,131 B2 | 3/2011 | Nakagawa et al. | |
| 7,932,188 B2 | 4/2011 | Lukas et al. | |
| 7,943,531 B2 | 5/2011 | Nemani et al. | |
| 8,449,942 B2 | 5/2013 | Liang et al. | |
| 8,481,403 B1 | 7/2013 | Gauri et al. | |
| 8,575,040 B2 | 11/2013 | Fucsko et al. | |
| 8,580,697 B1 | 11/2013 | Lang et al. | |
| 8,629,067 B2 | 1/2014 | Liang et al. | |
| 8,685,867 B1 | 4/2014 | Danek et al. | |
| 8,741,788 B2 | 6/2014 | Liang et al. | |
| 9,061,317 B2 | 6/2015 | Vrtis et al. | |
| 9,212,420 B2 | 12/2015 | Lee et al. | |
| 2002/0001973 A1* | 1/2002 | Wu ................. | C09C 1/3081 |
| | | | 438/780 |
| 2003/0064154 A1 | 4/2003 | Laxman et al. | |
| 2012/0142198 A1 | 6/2012 | Wang et al. | |
| 2013/0230987 A1 | 9/2013 | Draeger et al. | |
| 2013/0260575 A1 | 10/2013 | Al-Rashid et al. | |
| 2014/0073144 A1 | 3/2014 | Chatterjee et al. | |
| 2014/0302690 A1 | 10/2014 | Underwood et al. | |
| 2015/0368803 A1 | 12/2015 | Yim et al. | |
| 2016/0126089 A1 | 5/2016 | Liang et al. | |
| 2016/0138161 A1 | 5/2016 | Chen et al. | |

* cited by examiner

*Primary Examiner* — Kuo Liang Peng
(74) *Attorney, Agent, or Firm* — Michael K. Boyer; David K. Benson

(57) ABSTRACT

A method for depositing a silicon-containing film, the method comprising: placing a substrate comprising at least one surface feature into a flowable CVD reactor which is at a temperature of from about −20° C. to about 400° C.; introducing into the reactor at least one silicon-containing compound having at least one acetoxy group to at least partially react the at least one silicon-containing compound to form a flowable liquid oligomer wherein the flowable liquid oligomer forms a silicon oxide coating on the substrate and at least partially fills at least a portion of the at least one surface feature. Once cured, the silicon oxide coating has a low k and excellent mechanical properties.

9 Claims, 4 Drawing Sheets

PRECURSORS AND FLOWABLE CVD METHODS FOR MAKING LOW-K FILMS TO FILL SURFACE FEATURES

This Application claims the benefit of Application No. 62/381,222, filed on Aug. 30, 2016. The disclosure of Application No. 62/381,222 is hereby incorporated by reference.

BACKGROUND

Described herein is a process for the fabrication of an electronic device. More specifically, described herein are compositions for forming a silicon-containing film in a deposition process, such as, for example, a flowable chemical vapor deposition. Exemplary silicon-containing films that can be deposited using the compositions and methods described herein include silicon oxide, silicon nitride, silicon oxynitride or carbon-doped silicon oxide or carbon-doped silicon nitride films.

Flowable oxide deposition methods typically use alkoxysilane compounds as precursors for silicon-containing films which are deposited by controlled hydrolysis and condensation reactions. Such films can be deposited onto a substrate, for example, by applying a mixture of water and alkoxysilanes, optionally with solvent and/or other additives such as surfactants and porogens, onto a substrate. Typical methods for the application of these mixtures include spin coating, dip coating, spray coating, screen printing, co-condensation, and ink jet printing. After application to the substrate and upon application of one or more energy sources such as, for example, thermal, plasma, and/or other sources, the water within the mixture can react with the alkoxysilanes to hydrolyze the alkoxide and/or aryloxide groups and generate silanol species, which further condense with other hydrolyzed molecules and form an oligomeric or network structure.

Besides physical deposition or application of the precursor to the substrate, vapor deposition processes using water and a silicon containing vapor source for flowable dielectric deposition (FCVD) have been described, for instance, in U.S. Pat. Nos. 7,541,297; 8,449,942; 8,629,067; 8,741,788; 8,481,403; 8,580,697; 8,685,867; 7,498,273; 7,074,690; 7,582,555; 7,888,233, and 7,915,131, as well as U.S. Publ. No. 2013/0230987 A1, the disclosures of which are incorporated herein by reference. Typical methods generally relate to filling gaps on substrates with a solid dielectric material by forming a flowable liquid film in the gap. The flowable film is formed by reacting a dielectric precursor which may have a Si—C bond with an oxidant to form the dielectric material. In certain embodiments, the dielectric precursor condenses and subsequently reacts with the oxidant to form dielectric material. In certain embodiments, vapor phase reactants react to form a condensed flowable film. Since the Si—C bond is relatively inert towards reaction with water, the resultant network may be beneficially functionalized with organic functional groups which impart desired chemical and physical properties to the resultant film. For example, the addition of carbon to the network may lower the dielectric constant of the resultant film.

Another approach to depositing a silicon oxide film using flowable chemical vapor deposition process is gas phase polymerization. For example, the prior art has focused on using compounds such as trisilylamine (TSA) to deposit Si, H, N containing oligomers that are subsequently oxidized to SiOx films using ozone exposure. Examples of such approaches include: U.S. Publ. No. 2014/0073144; U. S. Publ. No. 2013/230987; U.S. Pat. Nos. 7,521,378, 7,557, 420, and 8,575,040; and 7,825,040, the disclosures of which are incorporated herein by reference.

Regarding the processes that employ trisilylamine (TSA), TSA is typically delivered into the reaction chamber as a gas, mixed with ammonia, and activated in a remote plasma reactor to generate $NH_2$, NH, H and or N radicals or ions. The TSA reacts with the plasma activated ammonia and begins to oligomerize to form higher molecular weight TSA dimers and trimers or other species which contain Si, N and H. The substrate is placed in the reactor and cooled to one or more temperatures ranging from about 0 to about 50° C. at a certain chamber pressures and TSA/activated ammonia mixtures the oligomers begin to condense on the wafers surface in such a way that they can "flow" to fill the trench surface feature. In this way, a material which contains Si, N and H is deposited onto the wafer and fills the trench. In certain embodiments, a pre-anneal step is performed to allow the film to be more SiN-like. It is desirable to have a SiN material because the next process step is oxidation at one or more temperatures ranging from 100-700° C. using ozone or water. Because of the SiN bond distance and angles, it is known that as SiN is oxidized to $SiO_2$ there is a unit cell volume increase which prevents the film from shrinking.

Despite the recent activity in the art related to flowable chemical vapor deposition and other film deposition processes, problems still remain. One of these problems is related to film composition. For example, flowable oxide films deposited from the precursor trisilylamine (TSA) in a gas phase polymerization process yield films with a high density of Si—H bonds and have a wet etch rates in dilute HF solutions that are 2.2 to 2.5 times faster than high quality thermal oxide. Such films are not suitable for low-k film applications.

In many circumstances, a hardening process, including thermal annealing, UV cure, or ion/radical densification, may be applied to the flowable films. The hardening process may remove carbon groups, hydroxyl groups and smaller molecular weight species from the deposited materials. Referring now to FIG. 1, this often leaves voids, cracks or spaces in the hardened material. Such films are also not suitable for low-k film applications.

Thus, there is a need to provide alternative precursor compounds to produce silicon-containing films via flow CVD techniques that have the mechanical integrity and porosity to successfully function as low-k silicon oxide containing film material.

SUMMARY

The compositions or formulations described herein and methods using same overcome the problems of the prior art by depositing a silicon-containing film on at least a portion of the substrate surface that provides desirable film properties upon post-deposition treatment. The instant invention can provide a silicon containing film having: i) a mechanical integrity in terms of Young's Modulus from about 2 to about 15 GPa, about 4 to about 12 and in some cases about 6 to about 10, ii) a porosity of about 10 to about 30 volume %, about 12 to about 25 and in some cases about 16 to about 22 (e.g., as measured by eliposmetric porosimetry), and iii) a dielectric constant of about 2.2 to about 3.0, about 2.4 to about 2.8 and in some cases about 2.5 to about 2.7.

In one aspect, the invention described herein provides a method for depositing a silicon-containing film, the method comprising: placing a substrate comprising at least one surface feature into a reactor which is at a temperature of from about −20° C. to about 400° C.; introducing into the reactor at least one silicon-containing compound having at least one acetoxy group, wherein the at least one silicon-containing compound is selected from the group consisting of:

I(a). Acyloxysilanes with a formula of $(RCOO)_m R^1{}_n SiH_p$ wherein R is selected from hydrogen, a linear or branched $C_1$ to $C_6$ alkyl group; $R^1$ is selected from a linear or branched $C_1$ to $C_6$ alkyl group, a linear or branched $C_2$ to $C_6$ alkenyl group, a linear or branched $C_2$ to $C_6$ alkynyl group; m=2 or 3; n=1 or 2; p=0 or 1; and m+n+p=4;

I(b). Acyloxyalkoxysilanes with a formula of $(RCOO)_m (R^2O)_n SiH_p R^1{}_q$ wherein R is selected from hydrogen, a linear or branched $C_1$ to $C_6$ alkyl group; $R^1$ is selected from a linear or branched $C_1$ to $C_6$ alkyl group, a linear or branched $C_2$ to $C_6$ alkenyl group, a linear or branched $C_2$ to $C_6$ alkynyl group; $R^2$ is selected from a linear or branched $C_1$ to $C_6$ alkyl group; m=2 or 3; m=1 or 2; p=0 or 1; q=0 or 1 and m+n+p+q=4; and I(c). Acyloxyaminoxysilanes with a formula of $(RCOO)_m (R^3 R^4 NO)_n SiH_p R^1{}_q$ wherein R is selected from hydrogen, a linear or branched $C_1$ to $C_6$ alkyl group; $R^1$ is selected from a linear or branched $C_1$ to $C_6$ alkyl group, a linear or branched $C_2$ to $C_6$ alkenyl group, a linear or branched $C_2$ to $C_6$ alkynyl group; and $R^3$ is selected from hydrogen, a linear or branched $C_1$ to $C_{10}$ alkyl group; $R^4$ is selected from a linear or branched $C_1$ to $C_6$ alkyl group; m=2 or 3; n=1 or 2; p=0 or 1; q=0 or 1 and m+n+p+q=4; and providing a plasma into the reactor to at least partially react the at least one silicon-containing compound to form a flowable liquid oligomer wherein the flowable liquid oligomer forms a coating on the substrate and at least partially fills at least a portion of the at least one surface feature.

In another aspect, the method of the present invention further comprises the step of subjecting the coating to a thermal treatment at one or more temperatures between about 100° C. to about 1000° C. to densify at least a portion of the coating and form a hardened layer.

In still another aspect, the method of the present invention further comprises the step of exposing the hardened layer to energy selected from the group consisting of a plasma, infrared light, chemical treatment, an electron beam, or UV light to form the final silicon-containing film.

Another aspect of the invention relates to a precursor composition comprising at least one silicon-containing compound having at least one acetoxy group, wherein the at least one silicon-containing compound is selected from the group consisting of: I(a). Acyloxysilanes with a formula of $(RCOO)_m R^1{}_n SiH_p$ wherein R is selected from hydrogen, a linear or branched $C_1$ to $C_6$ alkyl group; $R^1$ is selected from a linear or branched $C_1$ to $C_6$ alkyl group, a linear or branched $C_2$ to $C_6$ alkenyl group, a linear or branched $C_2$ to $C_6$ alkynyl group; m=2 or 3; n=1 or 2; p=0 or 1; and m+n+p=4;

I(b). Acyloxyalkoxysilanes with a formula of $(RCOO)_m (R^2O)_n SiH_p R^1{}_q$ wherein R is selected from hydrogen, a linear or branched $C_1$ to $C_6$ alkyl group; $R^1$ is selected from a linear or branched $C_1$ to $C_6$ alkyl group, a linear or branched $C_2$ to $C_6$ alkenyl group, a linear or branched $C_2$ to $C_6$ alkynyl group; $R^2$ is selected from a linear or branched $C_1$ to $C_6$ alkyl group; m=2 or 3; m=1 or 2; p=0 or 1; q=0 or 1 and m+n+p+q=4; and I(c). Acyloxyaminoxysilanes with a formula of $(RCOO)_m (R^3 R^4 NO)_n SiH_p R^1{}_q$ wherein R is selected from hydrogen, a linear or branched $C_1$ to $C_6$ alkyl group; $R^1$ is selected from a linear or branched $C_1$ to $C_6$ alkyl group, a linear or branched $C_2$ to $C_6$ alkenyl group, a linear or branched $C_2$ to $C_6$ alkynyl group; and $R^3$ is selected from hydrogen, a linear or branched $C_1$ to $C_{10}$ alkyl group; $R^4$ is selected from a linear or branched $C_1$ to $C_6$ alkyl group; m=2 or 3; n=1 or 2; p=0 or 1; q=0 or 1 and m+n+p+q=4.

Another aspect of the invention relates to a film obtained by the inventive method and composition.

Other features and advantages of the present invention will be apparent from the following more detailed description of the preferred embodiment, taken in conjunction with the accompanying drawings which illustrate, by way of example, the principles of the invention.

The embodiments and features of the present invention can be used alone or in combinations with each other.

BRIEF DESCRIPTION OF THE DRAWINGS

The present invention will hereinafter be described in conjunction with the appended figures wherein like numerals denote like elements.

DETAILED DESCRIPTION

Figure 1:
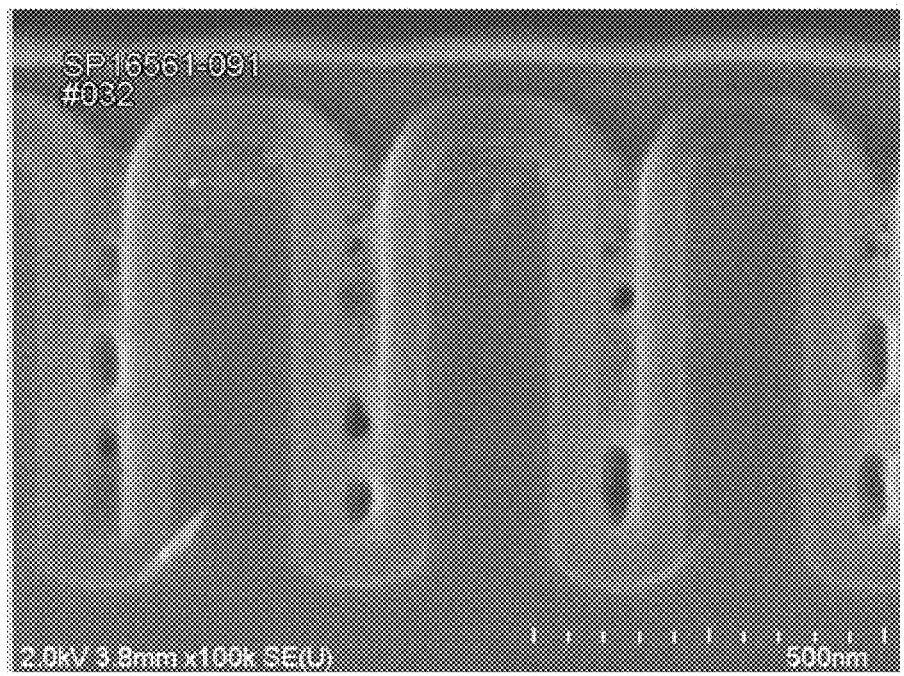
FIG. 1 is a SEM micrograph showing a silicon oxide film of the prior art formed in trenches of a substrate wherein voids formed during the hardening process.

The ensuing detailed description provides preferred exemplary embodiments only, and is not intended to limit the scope, applicability, or configuration of the invention. Rather, the ensuing detailed description of the preferred exemplary embodiments will provide those skilled in the art with an enabling description for implementing the preferred exemplary embodiments of the invention. Various changes may be made in the function and arrangement of elements without departing from the spirit and scope of the invention, as set forth in the appended claims.

In the claims, letters may be used to identify claimed method steps (e.g. a, b, and c). These letters are used to aid in referring to the method steps and are not intended to indicate the order in which claimed steps are performed, unless and only to the extent that such order is specifically recited in the claims.

The compositions or formulations described herein and methods using same overcome the problems of the prior art by depositing a silicon-containing film on at least a portion of the substrate surface that provides desirable film properties upon post-deposition treatment.

The present invention is directed to semiconductor thin film process techniques. Methods and system are described for improving quality of the dielectric film morphologically adapted over various device structures. More particularly, embodiments of the invention provide methods and systems of forming silicon oxide film with increased density to achieve void free gap fill for trenches having a high aspect ratio. For example, the invention is applied to form high quality silicon oxide films for filling narrow STI trenches, among other applications.

Accordingly, in one aspect, the present development provides a method for depositing a silicon-containing film, the method comprising: placing a substrate comprising at least one surface feature into a reactor which is at a temperature of from about −20° C. to about 400° C.; introducing into the reactor at least one silicon-containing compound having at least one acetoxy group, wherein the at least one silicon-containing compound is selected from the group consisting of:

I(a). Acyloxysilanes with a formula of $(RCOO)_m R^1_n SiH_p$ wherein R is selected from hydrogen, a linear or branched $C_1$ to $C_6$ alkyl group; $R^1$ is selected from a linear or branched $C_1$ to $C_6$ alkyl group, a linear or branched $C_2$ to $C_6$ alkenyl group, a linear or branched $C_2$ to $C_6$ alkynyl group; m=2 or 3; n=1 or 2; p=0 or 1; and m+n+p=4;

I(b). Acyloxyalkoxysilanes with a formula of $(RCOO)_m (R^2O)_n SiH_p R^1_q$ wherein R is selected from hydrogen, a linear or branched $C_1$ to $C_6$ alkyl group; $R^1$ is selected from a linear or branched $C_1$ to $C_6$ alkyl group, a linear or branched $C_2$ to $C_6$ alkenyl group, a linear or branched $C_2$ to $C_6$ alkynyl group; $R^2$ is selected from a linear or branched $C_1$ to $C_6$ alkyl group; m=2 or 3; m=1 or 2; p=0 or 1; q=0 or 1 and m+n+p+q=4; and I(c). Acyloxyaminoxysilanes with a formula of $(RCOO)_m (R^3R^4NO)_n SiH_p R^1_q$ wherein R is selected from hydrogen, a linear or branched $C_1$ to $C_6$ alkyl group; $R^1$ is selected from a linear or branched $C_1$ to $C_6$ alkyl group, a linear or branched $C_2$ to $C_6$ alkenyl group, a linear or branched $C_2$ to $C_6$ alkynyl group; and $R^3$ is selected from hydrogen, a linear or branched $C_1$ to $C_{10}$ alkyl group; $R^4$ is selected from a linear or branched $C_1$ to $C_6$ alkyl group; m=2 or 3; n=1 or 2; p=0 or 1; q=0 or 1 and m+n+p+q=4; and providing a plasma into the reactor to at least partially react the at least one silicon-containing compound to form a flowable liquid oligomer wherein the flowable liquid oligomer forms a coating on the substrate and at least partially fills at least a portion of the at least one surface feature.

By "flowable liquid oligomer" it is meant a polysiloxane material that is flowable under deposition conditions wherein the polysiloxane is measured via FTIR. After curing the flowable liquid oligomer forms a solid carbon doped porous OSG The silicon-containing film is selected from the group consisting of a silicon nitride, a silicon carbide, a silicon oxide, a carbon-doped silicon nitride, a silicon oxynitride, and a carbon-doped silicon oxynitride film. The compositions can be pre-mixed compositions, pre-mixtures (mixed before being used in the deposition process), or in-situ mixtures (mixed during the deposition process). Thus, in this disclosure the terms "mixture", "formulation", and "composition" are interchangeable.

Throughout the description, the term "silicon oxide" as used herein refers to a film comprising silicon and oxygen selected from the group consisting of stoichiometric or non-stoichiometric silicon oxide, carbon doped silicon oxide, silicon carboxynitride and there mixture thereof.

In the method of the present development, typically the first step is placing a substrate comprising at least one surface feature into a reactor which is at a temperature of from about −20° C. to about 400° C. Suitable substrates include, but are not limited to, semiconductor materials such as gallium arsenide ("GaAs"), boronitride ("BN") silicon, and compositions containing silicon such as crystalline silicon, polysilicon, amorphous silicon, epitaxial silicon, silicon dioxide ("$SiO_2$"), silicon carbide ("SiC"), silicon oxycarbide ("SiOC"), silicon nitride ("SiN"), silicon carbonitride ("SiCN"), organosilicate glasses ("OSG"), organofluorosilicate glasses ("OFSG"), fluorosilicate glasses ("FSG"), and other appropriate substrates or mixtures thereof. Substrates may further comprise a variety of layers to which the film is applied thereto such as, for example, antireflective coatings, photoresists, organic polymers, porous organic and inorganic materials, metals such as copper and aluminum, or diffusion barrier layers, e.g., TiN, Ti(C)N, TaN, Ta(C)N, Ta, W, WN, TiSiN, TaSiN, SiCN, TiSiCN, TaSiCN, or W(C)N. The organosilicate glass films of the present invention are preferably capable of adhering to at least one of the foregoing materials sufficiently to pass a conventional pull test, such as an ASTM D3359-95a tape pull test.

In some embodiments, the substrate may be a single crystal silicon wafer, a wafer of silicon carbide, a wafer of aluminum oxide (sapphire), a sheet of glass, a metallic foil, an organic polymer film or may be a polymeric, glass, silicon or metallic 3-dimensional article. The substrate may be coated with a variety of materials well known in the art including films of silicon oxide, silicon nitride, amorphous carbon, silicon oxycarbide, silicon oxynitride, silicon carbide, gallium arsenide, gallium nitride and the like. These coatings may completely coat the substrate, may be in multiple layers of various materials and may be partially etched to expose underlying layers of material. The surface may also have on it a photoresist material that has been exposed with a pattern and developed to partially coat the substrate.

In some embodiments, the substrate comprises a surface feature. The term "surface feature," as used herein, means that the substrate or partially fabricated substrate that comprises one or more of the following pores, trenches, shallow trench isolation (STI), vias, reentrant feature, or the like. In one particular embodiment, the surface feature(s) have a width of 100 µm or less, 1 µm in width or less, or 0.5 µm in width or less, or 50 nm in width or less. In this or other embodiments, the aspect ratio (the depth to width ratio) of the surface features, if present, is 0.1:1 or greater, or 1:1 or greater, or 10:1 or greater, or 20:1 or greater, or 40:1 or greater.

The method used to form the films or coatings described herein are flowable chemical deposition processes. Examples of suitable deposition processes for the method disclosed herein include, but are not limited to, thermal chemical vapor deposition (CVD) or plasma enhanced cyclic CVD (PECCVD) process. An exemplary flowable CVD reactor is disclosed in U.S. Publ. No. 2014/0073144; hereby incorporated by reference. As used herein, the term "flowable chemical vapor deposition processes" refers to any process wherein a substrate is exposed to one or more volatile precursors, which react and/or decompose on the substrate surface to provide flowable oligomeric silicon-containing species and then produce the solid film or material upon further treatment. Although the precursors, reagents and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator. In one embodiment, the films are deposited using a plasma-based (e.g., remote generated or in situ) CVD process. The term "reactor" as used herein, includes without limitation, a reaction chamber or deposition chamber.

In certain embodiments, the substrate may be exposed to one or more pre-deposition treatments such as, but not limited to, a plasma treatment, thermal treatment, chemical treatment, ultraviolet light exposure, electron beam exposure, and combinations thereof to affect one or more properties of the films. These pre-deposition treatments may occur under an atmosphere selected from inert, oxidizing, and/or reducing.

Although the chemical reagents used herein may be sometimes described as "gaseous," it is understood that the chemical reagents may be delivered directly as a gas to the reactor, delivered as vapors from vaporizing liquid or bubbling liquid using carrier gas such as nitrogen, helium or argon, vapors from subliming solid and/or transported by an inert carrier gas into the reactor.

The method of the present development includes the step of introducing into the reactor a silicon-containing compound (also referred to herein as a "precursor") having at least one acetoxy group wherein the at least one second compound is selected from the group consisting of the following Formula I(a) to I(c):

I(a). Acetoxysilanes with a formula of $(RCOO)_m R^1_n SiH_p$ wherein R and $R^1$ are independently selected from a linear or branched $C_1$ to $C_6$ alkyl group; m=2 or 3; n=1 or 2; p=0 or 1; and m+n+p=4;

I(b). Acetoxyalkoxysilanes with a formula of $(RCOO)_m (R1O)_n SiH_p$ wherein R and $R^1$ are independently selected from a linear or branched $C_1$ to $C_6$ alkyl group; m=2 or 3; m=1 or 2; p=0 or 1; and m+n+p=4; and I(c). Acetoxyaminoxysilanes with a formula of $(RCOO)_m (R^2 R^3 NO)_n SiH_p$ wherein R is selected from a linear or branched $C_1$ to $C_6$ alkyl group; $R^2$ is selected from hydrogen, a branched $C_1$ to $C_{10}$ alkyl group, and a $C_4$ to $C_{10}$ aryl group; and $R^3$ is selected from a linear or branched $C_1$ to $C_{10}$ alkyl group; m=2 or 3; n=1 or 2; p=0 or 1; and m+n+p=4.

In the formulae above and throughout the description, the term "linear alkyl" denotes a linear functional group having from 1 to 10, 3 to 10, or 1 to 6 carbon atoms. In the formulae above and throughout the description, the term "branched alkyl" denotes a linear functional group having from 3 to 10, or 1 to 6 carbon atoms. Exemplary linear alkyl groups include, but are not limited to, methyl, ethyl, propyl, butyl, pentyl, and hexyl groups. Exemplary branched alkyl groups include, but are not limited to, isopropyl, isobutyl, sec-butyl, tert-butyl, iso-pentyl, tert-pentyl, isohexyl, and neohexyl. In certain embodiments, the alkyl group may have one or more functional groups such as, but not limited to, an alkoxy group, a dialkylamino group or combinations thereof, attached thereto. In other embodiments, the alkyl group does not have one or more functional groups attached thereto. The alkyl group may be saturated or, alternatively, unsaturated.

In the formulae above and throughout the description, the term "aryl" denotes an aromatic cyclic functional group having from 3 to 10 carbon atoms, from 5 to 10 carbon atoms, or from 6 to 10 carbon atoms. Exemplary aryl groups include, but are not limited to, phenyl, benzyl, chlorobenzyl, tolyl, and o-xylyl.

In the formulae above and throughout the description, the term "alkenyl group" denotes a group which has one or more carbon-carbon double bonds and has from 2 to 12, from 2 to 10, or from 2 to 6 carbon atoms. Exemplary alkenyl groups include, but are not limited to, vinyl or allyl groups.

The term "alkynyl group" denotes a group which has one or more carbon-carbon triple bonds and has from 2 to 10 or from 2 to 6 carbon atoms. Exemplary alkenyl groups include, but are not limited to, ethynyl.

In certain embodiments, one or more of the alkyl group or aryl groups in the formulae may be "substituted" or have one or more atoms or group of atoms substituted in place of, for example, a hydrogen atom. Exemplary substituents include, but are not limited to, oxygen, sulfur, halogen atoms (e.g., F, Cl, I, or Br), nitrogen, alkyl groups, and phosphorous. In other embodiments, one or more of the alkyl group, alkenyl group, alkynyl group, aromatic and/or aryl group in the formulae may be unsubstituted.

In certain embodiments, any one or more of substituents $R^1$, $R^2$, and $R^3$ in the formulae described above can be linked with a C—C bond in the above formula to form a ring structure when they are not hydrogen. As the skilled person will understand, the substituent may be selected from a linear or branched $C_1$ to $C_{10}$ alkylene moiety; a $C_2$ to $C_{12}$ alkenylene moiety; a $C_2$ to $C_{12}$ alkynylene moiety; a $C_4$ to $C_{10}$ cyclic alkyl moiety; and a $C_6$ to $C_{10}$ arylene moiety. In these embodiments, the ring structure can be unsaturated such as, for example, a cyclic alkyl ring, or saturated, for example, an aryl ring. Further, in these embodiments, the ring structure can also be substituted or substituted. In other embodiments, any one or more of substituents $R^1$, $R^2$ and $R^3$ are not linked.

In embodiments wherein the silicon-containing precursor comprises a compound having Formula I(a), examples of precursors include the following:

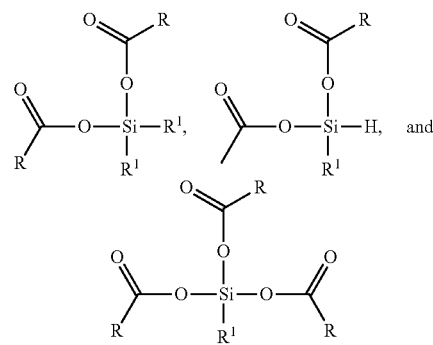

Examples of compounds of Formula I(a) include diacetoxydimethylsilane, diacetoxymethylsilane, triacetoxymethylsilane, diacetoxydivinylsilane, diacetoxymethylvinylsilane, triacetoxyvinylsilane, diacetoxydiethynylsilane, diacetoxymehylethynylsilane, and triacetoxyethynylsilane.

In embodiments wherein the silicon-containing precursor comprises a compound having Formula I(b), examples of precursors include the following:

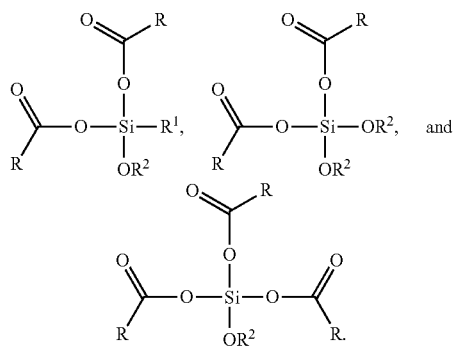

Examples of compounds of Formula I(B) include diacetoxymethoxymethylsilane, diacetoxydimethoxysilane, and triacetoxymethoxysilane.

In embodiments wherein the silicon-containing precursor comprises a compound having Formula I(c):

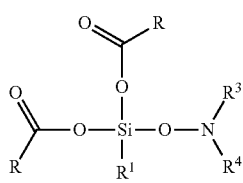

Examples of compounds of Formula I(c) include diacetoxydimethylaminoxymethylsilane, diacetoxydi(methylethyl)aminoxymethylsilane, and diacetoxydiethylaminoxymethylsilane.

The silicon-containing precursor compounds described herein may be delivered to the reaction chamber such as a CVD or ALD reactor in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, which leads to reproducible transport and deposition without thermal decomposition of the precursor. In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

The silicon-containing precursor compounds are preferably substantially free of halide ions such as chloride or metal ions such as Al. As used herein, the term "substantially free" as it relates to halide ions (or halides) or metal ions such as, for example, chlorides, fluorides, bromides, iodides, $Al^{3+}$ ions, $Fe^{2+}$, $Fe^{3+}$, $Ni^{2+}$, $Cr^{3+}$ means less than 5 ppm (by weight), preferably less than 3 ppm, and more preferably less than 1 ppm, and most preferably 0 ppm of each halide or metal ions. Chlorides or metal ions are known to act as decomposition catalysts for silicon precursors. Significant levels of chloride in the final product can cause the silicon precursors to degrade. The gradual degradation of the silicon precursors may directly impact the film deposition process making it difficult for the semiconductor manufacturer to meet film specifications. In addition, the shelf-life or stability is negatively impacted by the higher degradation rate of the silicon precursors thereby making it difficult to guarantee a 1-2 year shelf-life. Moreover, silicon precursors are known to form flammable and/or pyrophoric gases upon decomposition such as hydrogen and silane. Compositions comprising the instant precursor compounds are substantially free of such decomposition products. Therefore, the accelerated decomposition of the silicon-containing precursors presents safety and performance concerns related to the formation of these flammable and/or pyrophoric gaseous byproducts.

Silicon-containing precursors according to the present invention that are substantially free of halides can be achieved by (1) reducing or eliminating chloride sources during chemical synthesis, and/or (2) implementing an effective purification process to remove chloride from the crude product such that the final purified product is substantially free of chlorides. Chloride sources may be reduced during synthesis by using reagents that do not contain halides such as chlorodisilanes, bromodisilanes, or iododisilanes thereby avoiding the production of by-products that contain halide ions. In addition, the aforementioned reagents should be substantially free of chloride impurities such that the resulting crude product is substantially free of chloride impurities. In a similar manner, the synthesis should not use halide based solvents, catalysts, or solvents which contain unacceptably high levels of halide contamination. The crude product may also be treated by various purification methods to render the final product substantially free of halides such as chlorides. Such methods are well described in the prior art and, may include, but are not limited to purification processes such as distillation, or adsorption. Distillation is commonly used to separate impurities from the desire product by exploiting differences in boiling point. Adsorption may also be used to take advantage of the differential adsorptive properties of the components to effect separation such that the final product is substantially free of halide. Adsorbents such as, for example, commercially available $MgO$—$Al_2O_3$ blends can be used to remove halides such as chloride.

For those embodiments relating to a composition comprising a solvent(s) and at least one silicon-containing compound described herein, the solvent or mixture thereof selected does not react with the silicon compound. The amount of solvent by weight percentage in the composition ranges from 0.5% by weight to 99.5% or from 10% by weight to 75%. In this or other embodiments, the solvent has a boiling point (b.p.) similar to the b.p. of the precursors of Formulae I(a), I(b), and I(c) or the difference between the b.p. of the solvent and the b.p. of the silicon precursor precursors of Formulae I(a), I(b), and I(c) is 40° C. or less, 30° C. or less, or 20° C. or less, 10° C. or less, or 5° C. or less. Alternatively, the difference between the boiling points ranges from any one or more of the following end-points: 0, 10, 20, 30, or 40° C. Examples of suitable ranges of b.p. difference include without limitation, 0° C. to 40° C., 20° C. to 30° C., or 10° C. to 30° C. Examples of suitable solvents in the compositions include, but are not limited to, an ether (such as 1,4-dioxane, dibutyl ether), a tertiary amine (such as pyridine, 1-methylpiperidine, 1-ethylpiperidine, N,N'-Dimethylpiperazine, N,N,N',N'-Tetramethylethylenediamine), a nitrile (such as benzonitrile), an alkyl hydrocarbon (such as octane, nonane, dodecane, ethylcyclohexane), an aromatic hydrocarbon (such as toluene, mesitylene), a tertiary aminoether (such as bis(2-dimethylaminoethyl) ether), or mixtures thereof.

In one particular embodiment, the introducing step, wherein the at least one silicon-containing compound is introduced into the reactor, is conducted at one or more temperatures ranging from −20° C. to 1000° C., or from about 400° C. to about 1000° C., or from about 400° C. to about 600° C., or from about −20° C. to about 400° C. In these or other embodiments, the substrate comprises a semiconductor substrate comprising a surface feature.

The method of the present invention includes the step of providing an in-situ plasma or remote plasma source to at least partially react the at least one silicon-containing compound to form a flowable liquid oligomer wherein the flowable liquid oligomer forms a coating on the substrate and at least partially fills at least a portion of the at least one surface feature. Energy is applied to the at least one silicon-containing compound, nitrogen-containing source (if employed), oxygen source, other precursors or combination thereof to induce reaction and to form the silicon-containing film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

The volume flow ratio of precursor to oxygen or nitrogen containing source can range from about 40:1 to about 0.2:1, about 20:1 to about 1:1 and in some cases about 6:1 to about 2:1. In one embodiment of the invention, a composition comprises the inventive silicon containing precursor and at least one of the oxygen or nitrogen containing source. In another embodiment of the invention, a composition comprises an oligomer obtained from the inventive precursor and at least one of oxygen or nitrogen containing source.

In one particular embodiment, the plasma is selected from but not limited to the group consisting of a nitrogen plasma; plasma comprising nitrogen and helium; a plasma comprising nitrogen and argon; an ammonia plasma; a plasma comprising ammonia and helium; a plasma comprising ammonia and argon; helium plasma; argon plasma; hydrogen plasma; a plasma comprising hydrogen and helium; a plasma comprising hydrogen and argon; a plasma comprising ammonia and hydrogen; an organic amine plasma; a plasma comprising oxygen; a plasma comprising oxygen and hydrogen, and mixtures thereof.

In another embodiment, the plasma source is selected from but not limited to the group consisting of a carbon source plasma, including a hydrocarbon plasma, a plasma comprising hydrocarbon and helium, a plasma comprising hydrocarbon and argon, carbon dioxide plasma, carbon monoxide plasma, a plasma comprising hydrocarbon and hydrogen, a plasma comprising hydrocarbon and a nitrogen source, a plasma comprising hydrocarbon and an oxygen source, and mixture thereof.

As previously mentioned, the method deposits a film upon at least a portion of the surface of a substrate comprising a surface feature. The substrate is placed into the reactor and the substrate is maintained at one or more temperatures ranging from about −20° C. to about 400° C. In one particular embodiment, the temperature of the substrate is less than the walls of the chamber. The substrate temperature is held at a temperature below 100° C., preferably at a temperature below 25° C. and most preferably below 10° C. and greater than −20° C.

In certain embodiments, the reactor is at a pressure below atmospheric pressure or 750 torr ($10^5$ Pascals (Pa)) or less, or 100 torr (13332 Pa) or less. In other embodiments, the pressure of the reactor is maintained at a range of about 0.1 torr (13 Pa) to about 10 torr (1333 Pa).

In the presence of the plasma energy, the silicon-containing compounds react with each other and form oligomers which condense as a liquid (liquid oligomers) on the surface of the substrate and at least partially fill the features on the substrate. However, direct use of the as-deposited film can result in a dielectric that is too porous and does not have an adequate mechanical strength. Thus, certain embodiments of the present development are applied to perform further treatment of the as-deposited silicon oxide layer to improve film quality with increased density and still achieve a void free gap fill. By "void free" it is meant a visual determination obtained by viewing an SEM or TEM of the deposited and cured film.

In preferred embodiments, the flowable liquid oligomer is thermally annealed at one or more temperatures ranging from about 100° C. to about 1000° C. to densify at least a portion of the materials followed by broadband UV treatment at the temperature ranging from 100° C. to 1000° C.

To prevent voiding formation, cross-linking is needed during the treatment. For example, when diacetoxydimethylsilane is heated, an acetic anhydride molecule is lost and Si—O—Si bonds are formed. The loss of an acetic anhydride molecule leads to the creation and nanoscale pores. Since there are two acetoxy groups on each silicon atom, the cross-linking formation leads to long chains. To create 3-D cross-linking, a precursor with three acetoxy functional groups is needed. In other embodiments, an oxidant ($O_2$ or $CO_2$) is preferably added to create 3-D cross-linking. Film densities typically range from 1.5 to 2.0 $g/cm^3$ for silicon oxide or carbon doped silicon oxide and 1.8 to 2.8 $g/cm^3$ for silicon nitride or carbon doped silicon nitride. Thus, such films are suitable for use as low-k material applications. The dielectric constant, k, achieved typically ranges from 2.5 to 2.8, or 2.5 to 3.0, for carbon doped silicon oxide.

In certain embodiments, the resultant silicon-containing films or coatings can be exposed to a post-deposition treatment such as, but not limited to, a plasma treatment including, but not limited to, hydrogen plasma, helium plasm, argon plasma, ammonia plasma, water ($H_2O$) plasma, oxygen plasma, ozone ($O_3$) plasma, NO plasma, $N_2O$ plasma, carbon monoxide (CO) plasma, carbon dioxide ($CO_2$) plasma and combinations thereof, chemical treatment, ultraviolet light exposure, infrared exposure, electron beam exposure, and/or other treatments to affect one or more properties of the film.

In some embodiments, the post thermal treatment materials are exposed to a plasma, infrared lights, chemical treatment, an electron beam, or UV light to form a dense film.

The above steps define one cycle for the methods described herein; and the cycle can be repeated until the desired thickness of a silicon-containing film is obtained. In this or other embodiments, it is understood that the steps of the methods described herein may be performed in a variety of orders, may be performed sequentially or concurrently (e.g., during at least a portion of another step), and any combination thereof. The respective step of supplying the compounds and other reagents may be performed by varying the duration of the time for supplying them to change the stoichiometric composition of the resulting silicon-containing film.

In one embodiment of the invention, at least one of the following films or features can be formed or deposited upon the inventive silicon containing film: i) subject to planarization, ii) copper (e.g., to fill vias), and iii) dielectric films. In one aspect, the instant invention comprises a substrate comprising patterned structure having at least one feature (e.g., via or trench) upon which the inventive film (e.g., carbon doped silicon oxide) is deposited and a film comprising a barrier layer (e.g., at least one of cobalt, silicon carbonitride, silicon nitride, carbon oxynitride, TiN and TaN) deposited upon the inventive film.

The following examples are provided for the purpose of further illustrating the present invention but are by no means intended to limit the same.

EXAMPLES

Flowable chemical vapor deposition (FCVD) films were deposited onto medium resistivity (8-12 Ωcm) single crystal silicon wafer substrates and Si pattern wafers. In certain examples, the resultant silicon-containing films or coatings can be exposed to a pre-deposition treatment such as, but not limited to, a plasma treatment, thermal treatment, chemical treatment, ultraviolet light exposure, Infrared exposure, electron beam exposure, and/or other treatments to affect one or more properties of the film.

Depositions on a modified FCVD chamber on an Applied Materials Precision 5000 system, can be performed using either a silane or a TEOS process kit. The chamber has direct liquid injection (DLI) delivery capability. The precursors are liquids with delivery temperatures dependent on the precursor's boiling point.

To deposit initial flowable carbon doped oxide films, typical liquid precursor flow rates were 100-5000 mg/min, oxygen (or alternatively carbon dioxide) flow rates were 20-40 sccm, in-situ plasma power density was 0.25-3.5 W/cm$^2$, pressure was 0.75-12 Torr. To densify the as-deposit flowable films, the films were thermally annealed and/or UV cured in vacuum using the modified PECVD chamber at 100~1000 C, preferably 300~400° C. Thickness and refractive index (RI) at 632 nm were measured by a SCI reflectometer or Woollam ellipsometer. Typical film thickness ranged from 10 to 2000 nm. Bonding properties and hydrogen content (Si—H, C—H and N—H) of the silicon-based films were measured and analyzed by a Nicolet transmission Fourier transform infrared spectroscopy (FTIR) tool. All density measurements were accomplished using X-ray reflectivity (XRR). X-ray Photoelectron Spectroscopy (XPS) and Secondary ion mass spectrometry (SIMS) analysis were performed to determine the elemental composition of the films. The flowability and gap fill effects on patterned wafers were observed by a cross-sectional Scanning Electron Microscopy (SEM) using a Hitachi S-4800 system at a resolution of 2.0 nm. The porosity of the film was measured by ellipsometric porosimetry.

Flowable CVD depositions were conducted using a design of experiment (DOE) methodology. The experimental design includes: precursor flows from 100 to 5000 mg/min, preferably 500 to 2000 mg/min; oxygen (or CO$_2$) flow from 0 sccm to 1000 sccm, preferably 0 to 100 sccm; pressure from 0.75 to 12 Torr, preferably 6 to 10 Torr; RF power (13.56 MHz) 50 to 1000 W, preferably 100~500 W; Low-frequency (LF) power 0 to 100 W; and deposition temperature ranged from −20 to 400° C., preferably −20° C. to 40° C. The DOE experiments were used to determine what process parameters produced the optimal film with good flowability.

Deposition of Low-K Film with Diacetoxydimethylsilane as Precursor

In this experiment, the process conditions used to deposit flowable porous low-k films with the most favorable film properties are as follows: power=200 W, spacing=200 mils, pressure=6~10 Torr, Temperature=30~35° C., diacetoxydimethylsilane=1500~2000 mg/min, He=200 sccm, O2=40~60 sccm. The flowable film was thermally annealed at 300° C. for 5 min, followed by 400° C. UV cure for 10 minutes.

Films with RI of 1.37 and k of 2.6~2.7 were obtained on blanket substrates. The porosity of the film was 19~20%. With the processing pressure at 8 Torr, the modulus of the film was 10.4 GPa; hardness was 1.84 GPa. The modulus and hardness were consistent with conventional PECVD porous low-k films.

Figure 2:
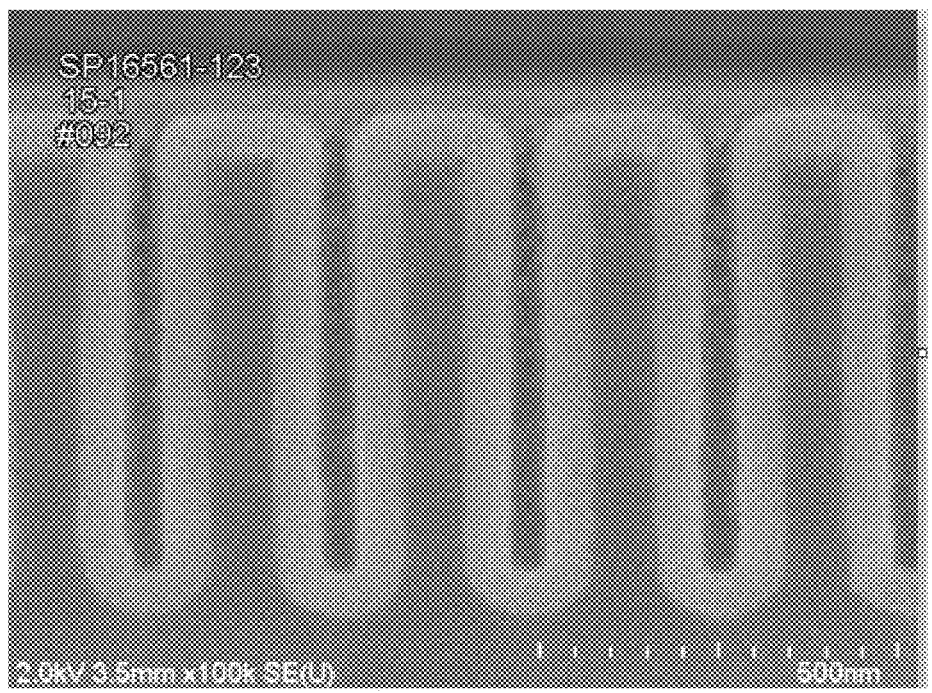
FIG. 2 is a SEM micrograph showing a silicon oxide film formed according to the process of the present invention via deposition of diacetoxydimethylsilane with 02.
Figure 3:
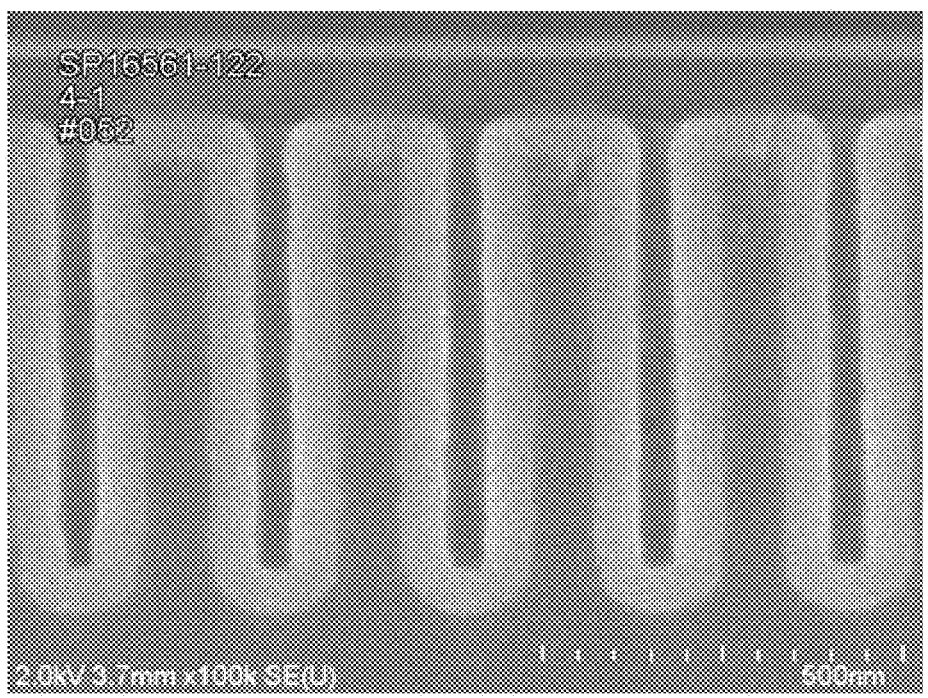
FIG. 3 is a SEM micrograph showing the silicon oxide film of FIG. 2 after thermal annealing at 300° C. for 5 min according to the process of the present invention.
Figure 4:
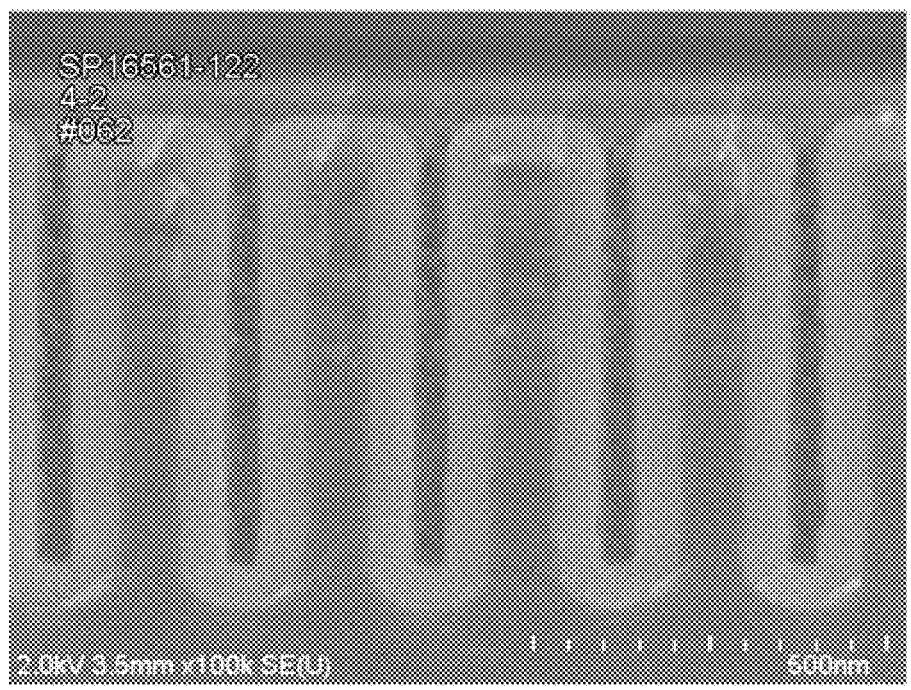
FIG. 4 is a SEM micrograph showing the silicon oxide film of FIG. 3 after UV exposure for 10 min at 400° C. according to the process of the present invention.

Referring now to FIG. 2, FIG. 2 shows a cross-sectional SEM indicates that good gap-fill was achieved by the deposition of diacetoxydimethylsilane with O$_2$. Referring now to FIG. 3, FIG. 3 shows a cross-sectional SEM of the film of FIG. 2 that was thermally annealed for 5 min at 300° C. and UV cured for 10 min at 400° C. (FIG. 4). Referring now to FIG. 4, FIG. 4 is a SEM micrograph showing the silicon oxide film of FIG. 3 after UV exposure for 10 min at 400° C.

While the principles of the invention have been described above in connection with preferred embodiments, it is to be clearly understood that this description is made only by way of example and not as a limitation of the scope of the invention.

The invention claimed is:

1. A method for depositing a silicon-containing film, the method comprising:
   placing a substrate comprising at least one surface feature into a reactor which is at a temperature of from about −20° C. to about 400° C.;
   introducing into the reactor at least one silicon-containing compound having at least one acyloxy group, wherein the at least one silicon-containing compound is an acyloxysilane having a structure:

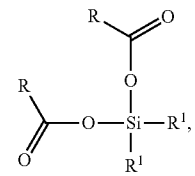

wherein R is selected from the group consisting of hydrogen, and a linear or branched $C_1$ to $C_6$ alkyl group; $R^1$ is selected from the group consisting of a linear or branched $C_1$ to $C_6$ alkyl group, a linear or branched $C_2$ to $C_6$ alkenyl group, and a linear or branched $C_2$ to $C_6$ alkynyl group; and providing an in-situ plasma or remote plasma source to the reactor to at least partially react the at least one silicon-containing compound to form a flowable liquid oligomer wherein the flowable liquid oligomer forms a coating on the substrate and at least partially fills at least a portion of the at least one surface feature.

2. The method of claim 1 wherein the plasma is selected from the group consisting of an in-situ or remote plasma source based plasma comprising nitrogen, an in-situ or remote plasma source based plasma comprising nitrogen and helium, an in-situ or remote plasma source based plasma comprising nitrogen and argon, an in-situ or remote plasma source based plasma comprising ammonia, an in-situ or remote plasma source based plasma comprising ammonia and helium, an in-situ or remote plasma source based plasma comprising ammonia and argon, helium plasma, argon plasma, hydrogen plasma, an in-situ or remote plasma source based plasma comprising hydrogen and helium, an in-situ or remote plasma source based plasma comprising hydrogen and argon, an in-situ or remote plasma source based plasms comprising ammonia and hydrogen, an in-situ or remote plasma source based organic amine plasma, an in-situ or remote plasma source based plasma comprising oxygen, an in-situ or remote plasma source based plasma comprising oxygen and hydrogen, and mixtures thereof.

3. The method of claim 1 further comprising the step of subjecting the coating to a thermal treatment at one or more temperatures between about 100° C. to about 1000° C. to densify at least a portion of the coating and form a hardened layer.

4. The method of claim 3 further comprising the step of exposing the hardened layer to energy selected from the group consisting of a plasma, infrared light, chemical treatment, an electron beam, or UV light to form the final silicon-containing film.

5. The method of claim 4 wherein the above steps define one cycle for the method and the cycle can be repeated until the desired thickness of the silicon-containing film is obtained.

6. The method of claim 1 wherein the at least one silicon-containing compound having at least one acetoxy group comprises diacetoxydimethylsilane.

7. The method of claim 1 wherein R is selected from the group consisting of methyl, ethyl, n-propyl, iso-propyl, tert-butyl, n-butyl, sec-butyl, and iso-butyl; and $R^1$ is selected from the group consisting of methyl, ethyl, vinyl, allyl, and ethynyl.

8. The method of claim 1 wherein the silicon containing film has a dielectric constant of <3.0 as determined by Capacitance-Voltage measurements, a porosity of >10% as measured by Ellipsometric Porosimetry.

9. A silicon containing film obtained by the method of claim 1 having a dielectric constant of <3.0 as determined by Capacitance-Voltage measurements, a porosity of >10 volume % as measured by Ellipsometric Porosimetry upon a substrate having at least one surface feature.

* * * * *